US005536495A

United States Patent [19]

Foster

[11] Patent Number: 5,536,495
[45] Date of Patent: Jul. 16, 1996

[54] USE OF G-CSF TO REDUCE ACUTE REJECTION

[76] Inventor: Preston F. Foster, 423 Lenox St., Oak Park, Ill. 60302

[21] Appl. No.: 228,143

[22] Filed: Apr. 15, 1994

[51] Int. Cl.$^6$ ..................................................... A61K 45/05
[52] U.S. Cl. ............................................ 424/851; 514/12
[58] Field of Search ............................. 424/85.1; 514/12

[56] References Cited

U.S. PATENT DOCUMENTS

| | | | |
|---|---|---|---|
| 4,810,643 | 3/1989 | Souza | 435/68 |
| 4,904,584 | 1/1990 | Shaw | 435/69.4 |
| 5,166,322 | 11/1992 | Shaw et al. | 530/351 |
| 5,194,592 | 3/1993 | Yoshida | 530/388.23 |
| 5,214,132 | 5/1993 | Kuga et al. | 530/351 |
| 5,218,092 | 6/1993 | Sasaki et al. | 530/351 |
| 5,241,072 | 8/1993 | Colon et al. | 548/218 |

FOREIGN PATENT DOCUMENTS

| | | |
|---|---|---|
| 76380/91 | 11/1991 | Australia . |
| 10948/92 | 8/1992 | Australia . |
| 0230980 | 8/1987 | European Pat. Off. . |
| 243153A2 | 10/1987 | European Pat. Off. . |
| 256843A1 | 2/1988 | European Pat. Off. . |
| 272703A1 | 6/1988 | European Pat. Off. . |
| 335423A2 | 10/1989 | European Pat. Off. . |
| 370205A2 | 5/1990 | European Pat. Off. . |
| 401384A1 | 12/1990 | European Pat. Off. . |
| 456200A1 | 11/1991 | European Pat. Off. . |
| 459630A2 | 12/1991 | European Pat. Off. . |
| 473268A2 | 3/1992 | European Pat. Off. . |
| 4164098 | 6/1992 | Japan . |
| WO89/05824 | 6/1989 | WIPO . |
| WO89/10932 | 11/1989 | WIPO . |
| WO90/06952 | 6/1990 | WIPO . |
| WO90/12874 | 11/1990 | WIPO . |
| WO91/05798 | 5/1991 | WIPO . |
| WO91/11520 | 8/1991 | WIPO . |
| WO91/18911 | 12/1991 | WIPO . |
| WO92/04455 | 3/1992 | WIPO . |
| WO92/06116 | 4/1992 | WIPO . |
| WO93/05169 | 3/1993 | WIPO . |
| WO93/15211 | 8/1993 | WIPO . |

OTHER PUBLICATIONS

Parenteau, G. L. et al., Transplantation, vol. 54(6), pp. 963–68, 1992.

Ishizone et al., J Pediatric Surgery, vol. 29(4), pp. 510–513, Apr. 1994.

Billingham, "Dilemma of Variety of Histopathologic Grading Systems for Acute Cardiac Allograft Rejection by Endomyocardial Biopsy", *J. Heart Transplant.*, 9:272–276 (1990).

Colquhoun et al., "Reversal of Neutropenia with Granulocyte Colony–Stimulating Factor without Precipitating Liver Allograft Rejection", *Transplantation*, 56:755–758 (1993).

Diflo et al., "Simultaneous use of Ganciclovir and Granulocyte Colony Stimulating Factor in Liver Transplant Recipients", *Hepatology*, 16:278A (1992).

Foster et al., "Blood and Graft Eosinophilia as Predictors of Rejection in Human Liver Transplantation", *Transplantation*, 47:72–74 (1989).

Gabrilove, "Introduction and Overview of Hematopoietic Growth Factors", *Seminars in Hematology*, 26:1–4 (1989).

Gorgen et al., "Granulocyte Colony–Stimulating Factor Treatment Protects Rodents Against Lipopolysaccharide–Induced Toxicity Via Suppression of Systemic Tumor Necrosis Factor–α", *J. Immunol.*, 149:918–924 (1992).

Jones et al., "Growth factors in haemopoiesis", *Balliere's Clinical Hematology*, 2:83–111 (1989).

Kuga et al., "Mutagenesis of Human Granulocyte Colony Stimulating Factor", *Biochem. Biophys. Res. Comm.*, 159:103–111 (1989).

Lachaux et al., "Treatment with lenograstim (glycosylated recombinant human granulocyte colony–stimulating factor) and orthotopic liver transplantation for glycogen storang disease type Ib", *J. Pediatrics*, 123:1005–1008 (1993).

Lu et al., "Disulfide and Secondary Structures of Recombinant Human Granulocyte Colony Stimulating Factor", *Arch. Biochem. Biophys.*, 268:81–92 (1989).

Moore et al., "Synergy of interleukin 1 and granulocyte colony–stimulating factor: In vivo stimulation of stem–cell recovery and hematopoietic regeneration following 5–fluorouracil treatment of mice", *Proc. Nat'l. Acad. Sci. (USA)*, 84:7134–7138 (1987).

Nagaata et al., "The chromosomal gene structure and two mRNAs for human granulocyte colony–stimulating factor", *EMBO J.*, 5:575–581 (1986).

Ono et al., "Improved technique of heart transplantation in rats", *J. Thoracic Cardiovasc. Surg.*, 57:225–229 (1969).

Paradis et al., "Distinguishing Between Infection, Rejection, and the Adult Respiratory Distress Syndrome After Human Lung Transplantation",*J. Heart Lung Transplant.*, 11:S232–236 (1992).

Souza et al., "Recombinant Human Granulocyte Colony–Stimulating Factor: Effects on Normal and Leukemic Myeloid Cells", *Science*, 232:61–65 (1986).

Welte et al., "Purification and biochemical characterization of human pluripotent hematopoietic colony–stimulating factor", *Proc. Nat'l. Acad. Sci. (USA)*, 82:1526–1530 (1985).

Williams et al., "Role of Liver Allograft Biopsy in Patient Management", *Seminars in Liver Disease*, 12:60–72 (1992).

Wright et al., "Granulocyte Colony–Stimulating Factor (GCSF) Combined with α Interferon (α IFN) for Treatment of Liver Allograft Recipients with Viral Hepatitis", *Hepatology*, 14:48A (1991).

Adams et al., "Neutrophil Activation—An Important Cause of Tissue Damage During Liver Allograft Rejection?," *Transplantation*, 50:86–91 (1990).

(List continued on next page.)

Primary Examiner—Chhaya D. Sayala
Attorney, Agent, or Firm—Marshall, O'Toole, Gerstein, Murray & Borun

[57] ABSTRACT

Reduction of occurrence of acute rejection of organ transplants is achieved by treatment with a G-CSF protein product.

3 Claims, No Drawings

OTHER PUBLICATIONS

Dale, "Alterations in Laboratory Findings—Section 11", in *Harrison's Principles of Internal Medicine*, p. 284, McGraw–Hill, New York (1980).

Foker et al., "Principles of Immunosuppression," in *Davis–Christopher Textbook of Surgery*, pp. 496–515, W. B. Saunders, Philadelphia, PA (1981).

Nery et al., "Incidence and Outcome of Acute Rejection in Liver Transplantation," *Transplantation Proc.*, XX(*3, Supp. 3*):375–377 (1988).

Reich, *Hematology*, p. 253, Little, Brown and Company, Boston (1978).

Tamaki et al., "Adverse Effect of rhG–CSF in the Process of Rat Heart Allograft Rejection." *Transplantation Proc.*, 26:2311–2312 (1994).

USE OF G-CSF TO REDUCE ACUTE REJECTION

BACKGROUND OF THE INVENTION

Organ transplants of liver, kidney, heart, and lung are now regularly performed now as treatment for end-stage organ disease. Allograft (same species donor and recipient) as well as xenograft (different species donor and recipient) transplants have been performed. Two primary problems for all organ transplants, however, have been acute rejection of the donor organ and the high risk of infection. Treatment for acute rejection, intensification of immunosuppression, causes deterioration of immune function, resulting in increased susceptibility to serious infection.

Organ transplants evoke a variety of immune responses in the recipient. In acute rejection, the graft is initially invaded by recipient mononuclear cells (macrophage, lymphocyte and monocyte cells). If these cells perceive antigenic differences in the graft, they will process and present the antigen to a T-lymphocyte and activate it in an antigen-specific manner. The T-cell then stimulates the central lymphoid system to elicit an immune response. The response is usually a combination of cellular (T-cell mediated) and humoral (B-cell mediated) responses. The former reaction appears to be the primary cause of the initial acute transplant rejection occurring one to three weeks post-transplant. The outcome of this acute rejection depends in part on whether immunosuppressive treatment is effective.

Acute rejection is reported to occur in 50 to 70% of hepatic grafts, depending on the criteria for diagnosis. Although quite common, few transplanted livers fail because of uncontrollable acute rejection. Relative ease of acute rejection control of hepatic grafts is not seen with other solid organ grafts, such as kidney, pancreas, and cardiac grafts.

In liver transplant patients, acute rejection is characterized by two consecutive days of rising bilirubin or liver enzymes (such as SGOT, SGPT, and alkaline phosphatase), which would indicate graft dysfunction, and simultaneous histologic findings of rejection on biopsy. The earliest histologic changes characteristic of acute rejection are accumulation of mononuclear cells in the portal tracts. The infiltrate consists of lymphocytes, and to a lesser extent neutrophils and eosinophils. Infiltrates that spill over into the parenchyma constitute a more specific sign of established acute rejection. The presence of eosinophils and the polymorphonuclear cells (PMNs) is often obscured by a prominent lymphocytic infiltrate. Eosinophilia and endothelialitis of the central vein and portal vein are also seen. Histologic evidence of biliary damage is reported to occur in 10 to 75% of patients with acute rejection. See Foster et al., *Transplantation*, 47:72–74 (1989) and Williams et al., *Seminars in Liver Disease*, 12:60–72 (1992).

In heart transplant patients, acute rejection is characterized by clinical signs of fever, arrhythmia, congestive heart failure, and increased cardiac volumes on echocardiogram. The diagnosis is established by transvenous endomyocardial biopsy using grading criteria published by Billingham, *J. Heart Transplant*, 9:272–276 (1990).

In lung transplant patients, acute rejection is characterized by clinical signs of fever, leukocytosis, bronchorrhea, and increasing alveolar to arteriolar oxygen gradient, all in the absence of pulmonary infection. Radiographic findings on chest X-ray may be normal or may show bi-perihilar infiltrates. Spirometry typically shows decreased forced expiratory volume over one second. The final diagnosis is established on clinical grounds, by response to bolus steroids, and on the basis of transbronchial biopsy. These criteria have been discussed in Paradis et al., *J. Heart and Lung Transplant*, 11:S232–6 (1992).

In kidney transplant patients, acute rejection is characterized by deteriorating renal function as shown by increasing BUN and creatinine, graft enlargement, fever, oliguria, hypertension, and reduced renal clearances. Renal scans will initially show a reduction in excretion with cortical retention, followed in several days by reductions in cortical uptake as well. If the rejection episode occurs during a period of acute tubular necrosis, its diagnosis may be delayed, being made either by serial scan assessment or by a transplant biopsy during a febrile episode. Lymphocymria is often found and may be helpful, along with a negative urine culture in ruling out graft pyelonephritis. Renal biopsies performed at this time typically reveal interstitial nephritis, mononuclear cell infiltrate, acute arteritis, and glomerular injury. Patients with multiple or severe early rejections have worse graft functional outcomes (at one, two, and five years) than patients without.

Granulocyte colony stimulating factor (G-CSF) is one of the hematopoietic growth factors, also called colony stimulating factors, that stimulate committed progenitor cells to proliferate and to form colonies of differentiating blood cells, G-CSF preferentially stimulates the growth and development of neutrophils, and is useful for treating in neutropenic states. Welte et al., *PNAS-USA* 82: 1526–1530 (1985); Souza et al., *Science* 232: 61–65 (1986) and Gabrilove, J. *Seminars in Hematology* 26: (2) 1–14 (1989). G-CSF increases the number of circulating granulocytes and has been reported to ameliorate infection in sepsis models. G-CSF administration also inhibits the release of tumor necrosis factor (TNF), a cytokine important to tissue injury during sepsis and rejection. See, e.g., Wendel et al., *J. Immunol.*, 149:918–924 (1992).

In humans, endogenous G-CSF is detectable in blood plasma. Jones et al., *Bailliere's Clinical Hematology* 2 (1): 83–111 (1989). G-CSF is produced by fibroblasts, macrophages, T cells trophoblasts, endothelial cells and epithelial cells and is the expression product of a single copy gene comprised of four exons and five introns located on chromosome seventeen. Transcription of this locus produces a mRNA species which is differentially processed, resulting in two forms of G-CSF mRNA, one version coding for a protein of 177 amino acids, the other coding for a protein of 174 amino acids. Nagata et al., *EMBO J* 5: 575–581 (1986). The form comprised of 174 amino acids has been found to have the greatest specific in vivo biological activity. G-CSF is species cross-reactive, such that when human G-CSF is administered to another mammal such as a mouse, canine or monkey, sustained neutrophil leukocytosis is elicited. Moore et al. *PNAS-USA* 84: 7134–7138 (1987).

Human G-CSF can be obtained and purified from a number of sources. Natural human G-CSF (nhG-CSF) can be isolated from the supernatants of cultured human tumor cell lines. The development of recombinant DNA technology has enabled the production of commercial scale quantities of G-CSF in glycosylated form as a product of eukaryotic host cell expression, and of G-CSF in non-glycosylated form as a product of prokaryotic host cell expression. See, e.g., U.S. Pat. No. 4,810,643 (Souza) incorporated herein by reference.

G-CSF has been found to be useful in the treatment of indications where an increase in neutrophils will provide benefits. For example, for cancer patients, G-CSF is beneficial as a means of selectively stimulating neutrophil production to compensate for hematopoietic deficits resulting from chemotherapy or radiation therapy. Other indications include treatment of various infectious diseases and related conditions, such as sepsis, which is typically caused by a metabolite of bacteria. G-CSF is also useful alone, or in combination with other compounds, such as other cytokines, for growth or expansion of cells in culture for example, for bone marrow transplants. G-CSF has been administered to transplant patients as an adjunct to treatment of infection or for treatment of neutropenia. See Diflo et al., *Hepatology*, 16:PA278 (1992), Wright et al., *Hepatology*, 14:PA48 (1991), Lachaux ell al., *J. Pediatrics*, 123:1005–1008 (1993), and Colquhoun et al., *Transplantation*, 56:755–758 (1993).

SUMMARY OF INVENTION

The present invention provides a method for reducing the occurrence of acute rejection of organ transplants in a patient comprising administering a therapeutically effective dose of G-CSF protein product. In preferred forms of practice of the invention, recombinant human G-CSF is administered in unit dosage forms of from 5 to 50 µg/kg on a daily basis.

DETAILED DESCRIPTION OF THE INVENTION

According to the present invention, administration of G-CSF protein product to subjects after organ transplantation results in a reduced rate of acute rejection of the organ transplant, as well as reduced infection rates and improved overall survival rates. Treatment according to the invention also results in reduced duration of stay under intensive care, reduced duration of ventilator treatment, and reduced incidence of acute respiratory distress syndrome (ARDS). G-CSF protein product can be administered intravenously according to the invention generally at dosages varying between 5 and 50 µg/kg/day over a period of 10 to 14 days. G-CSF protein product can also be administered via oral, pulmonary or other routes.

The term "G-CSF protein product" as used herein is defined as naturally occurring human and heterologous species G-CSF, recombinantly produced G-CSF that is the expression product consisting of either 174 or 177 amino acids, or fragments, analogs, variants, or derivatives thereof as reported, for example in Kuga et al., *Biochem. Biophy. Res. Comm* 159: 103–111 (1989); Lu et al., *Arch. Biochem. Biophys.* 268: 81–92 (1989); U.S. Pat. Nos. 4,810,643, 4,904,584, 5,214,132, and 5,218,092; EP 0 335423; EP 0 272703; EP 0 459630; EP 0 256843; EP 0 243153; WO 9102874; Australian Application document Nos. AU-A-10948/92 and AU-A- 76380/91. Included are chemically modified G-CSFs, see, e.g., those reported in WO 9012874, EP 0 401384 and EP 0 335423. See also, WO 9315211; WO 9305169; JP 04164098; WO 9206116; WO 9204455; EP O 473268; EP 0 456200; WO 9111520; WO 9105798; WO 9006952; WO 8910932; WO 8905824; WO 9118911; and EP O 370205.

The invention is better understood by reference to the following illustrative examples wherein: Example 1 demonstrates that, in human liver transplant patients, augmenting the usual treatment protocol with administration of a G-CSF protein product results in a statistically significant reduction in acute rejection rates and infection rates, in comparison to patients not treated with G-CSF; and Example 2 demonstrates that, in a rat heterotopic heart transplant model of acute rejection, administration of a G-CSF protein product to the rats, without other treatment, resulted in a statistically significant improvement in graft survival.

EXAMPLE 1

Recombinant human G-CSF Filgrastim (NEUPOGEN®, Amgen Inc., Thousand Oaks, Calif.) was administered to high-risk, adult liver transplant patients to study its effects on infection and rejection. Thirty-four consecutive liver allograft recipients were treated with G-CSF in addition to the usual protocol immunosuppressive therapy and were prospectively monitored over at least 120 days for sepsis and rejection outcomes. The data were compared to the previous forty-nine consecutive liver transplant patients who had not received G-CSF. The two groups were similar for age, sex, cause of liver failure, pre-op Childs-Turcotte grading, pre-op infection incidence and creatinine, United Network for Organ Sharing (UNOS) status, length of surgical procedure and blood components transfused.

All patients were treated pre-operatively with the antibiotics vancomycin and Claforan. Post-operatively, the antibiotic treatment was continued for 72 hours and the usual immunosuppressive regime was instituted. The usual immunosuppression protocol consists of 2.5 mg/kg Cyclosporine intravenously every twelve hours, regulated to maintain a blood level of cyclosporine at 200 to 400 ng/ml, and 1.5 mg/kg Solu-Medrol intravenously daily, with the dose decreasing by 10% every day until reaching a level of 0.35 mg/kg. At 7 to 10 days post-transplant, after the T-tube was clamped, the patients were switched to oral cyclosporine at a total dose of 10 to 15 mg/kg/day, divided in two doses and titrated to reach the same therapeutic blood level, and oral prednisone at 0.35 mg/kg/day.

Standard protocol diagnosis and treatment of infection and rejection was employed. Infection was diagnosed by (1) a temperature of greater than 101.5° F. or less than 96° F., (2) tachycardia, and (3) a specific site of infection as shown by positive sputum, blood, urine or wound cultures, and was treated with appropriate antibiotics. Acute rejection was diagnosed by serological and histological methods as described above and was treated with 1 g Solu-Medrol once a day for two consecutive days.

The G-CSF-treated patients also received human recombinant G-CSF intravenously at a dose of 5–10 µg/kg/day for 10 days postoperatively, with the dosage titrated to maintain a blood absolute granulocyte count (AGC) between 10,000 and 20,000 cells/mm$^3$. The outcome results are displayed in Table I below.

TABLE I

| Results | Controls (N = 49) | G-CSF (N-34) | Significance |
|---|---|---|---|
| AGC pre-op (× 10$^3$) | 4.4 ± 2.3 | 4.5 ± 2.3 | NS t-test |
| AGC peak post-op | 9.4 ± 4.5 | 20.5 ± 6.5 | $p < 0.0001$ t-test |
| ICU stay (days) | 20.5 ± 26.1 | 8.0 ± 11.8 | $p < 0.002$ t-test |
| Vent.time (days) | 17.3 ± 25.6 | 5.1 ± 8.2 | $p < 0.004$ t-test |
| ARDS | 37% | 11% | $p < 0.004$ $x^2$ |
| Acute rejection | 51% | 30% | $p < 0.02$ $x^2$ |
| Chronic rejection | 10% | 9% | NS $x^2$ |
| Infections/patient | 2.3 ± 2.8 | 1.5 ± 1.3 | $p < 0.006$ t-test |
| Survival (120 days) | 76% | 91% | $p < 0.06$ Breslow |

The G-CSF-treated patients had significantly reduced rates of infection (1.5 on average compared to 2.3 without G-CSF treatment) and acute rejection (30% compared to 51%, which was statistically significant using chi-square analysis).

EXAMPLE 2

The effect of G-CSF (Neupogen) treatment was investigated in the heterotopic rat heart transplant model described in Ono et al., *J. Thoracic Cardiovasc. Surg.*, 57:225 (1969). 24 Lewis rats underwent heterotopic heart transplantation from Brown-Norway donors and received varying, daily dosages of human recombinant G-CSF for 14 days postoperatively. No other treatment was administered except for G-CSF. Graft survival (days till cessation of graft heart beat), calculated using Breslow survival analysis, and AGC at six days post-operation were determined. Results are shown below in Table II.

TABLE II

| Results | N Graft Survival | Survival Avg. | AGC × $10^3$* |
|---|---|---|---|
| No treatment | 6 6,7,7,7,7,8 | 7.0 ± 0.6 | 3.8 ± 1.0 |
| G-CSF 20 µg/kg/day | 6 6,6,6,8,11,13 | 8.3 ± 3.0 | 2.9 ± 2.2 |
| G-CSF 250 µg/kg/day | 6 6,11,12,12,15,18 | 12.3 ± 4 | 7.2 ± 3.2 |
| G-CSF 500 µg/kg/day | 6 6,6,10,13,13,12 | 10.0 ± 3.2 | 14.9 ± 2.2 |

*The difference between G-CSF treatment and no treatment was determined with $p < 0.05$ using the Student t-test for groups with unknown distributions.

Treatment with G-CSF at 250 µg/kg/day resulted in a significant improvement in graft survival (an average of 12.3 days, compared to 7.0 days without G-CSF treatment). The improved graft survival observed with the G-CSF-treated rats corroborates the reduction in the incidence for acute rejection noted in our clinical study in human liver transplant patients.

What is claimed is:

1. A method for treating acute rejection in a non-granulocytopenic organ transplant patient comprising administering to the patient an amount of Granulocyte Colony Stimulating Factor (G-CSF) protein effective to reduce acute rejection.

2. A method for treating a non-granulocytopenic organ transplant patient comprising administering to the patient an amount of Granulocyte Colony Stimulating Factor (G-CSF) protein effective to reduce acute rejection.

3. The method of claims 1 or 2 wherein the amount of G-CSF protein administered is from 5 to 50 µg/kg/day.

* * * * *